United States Patent
Park et al.

(10) Patent No.: US 11,370,456 B2
(45) Date of Patent: Jun. 28, 2022

(54) SYSTEM AND METHOD FOR PROVIDING CUSTOMIZED RECOMMENDATION SERVICE USED FOR AUTONOMOUS VEHICLE

(71) Applicant: LG Electronics Inc., Seoul (KR)

(72) Inventors: Yong Soo Park, Seoul (KR); Hyong Guk Kim, Seoul (KR); Hyeong Jin Im, Seoul (KR); Jaehoon Cho, Seoul (KR); Hee Jeong Heo, Seoul (KR); Yoonjung Hong, Seoul (KR)

(73) Assignee: LG Electronics Inc., Seoul (KR)

( * ) Notice: Subject to any disclaimer, the term of this patent is extended or adjusted under 35 U.S.C. 154(b) by 360 days.

(21) Appl. No.: 16/490,226

(22) PCT Filed: Mar. 8, 2019

(86) PCT No.: PCT/KR2019/002760
§ 371 (c)(1),
(2) Date: Aug. 30, 2019

(87) PCT Pub. No.: WO2020/184742
PCT Pub. Date: Sep. 17, 2020

(65) Prior Publication Data
US 2021/0362748 A1 Nov. 25, 2021

(51) Int. Cl.
*B60W 60/00* (2020.01)
*G16H 20/30* (2018.01)
(Continued)

(52) U.S. Cl.
CPC ........ *B60W 60/0025* (2020.02); *B60W 40/04* (2013.01); *B60W 50/14* (2013.01);
(Continued)

(58) Field of Classification Search
CPC .................. B64C 13/503; B60W 60/0025
See application file for complete search history.

(56) References Cited

U.S. PATENT DOCUMENTS 9,776,042 B2 * 10/2017 Prokhorov .......... A63B 22/0025
9,787,818 B2 * 10/2017 Kwon .................... G16H 40/67
(Continued)

FOREIGN PATENT DOCUMENTS

DE 102016013829 A1 * 5/2017 ......... A63B 21/4047
JP 2016091411 5/2016
(Continued)

OTHER PUBLICATIONS

KR Notice of Allowance in Korean Application No. 10-2019-701962, dated Mar. 31, 2021, 12 pages (with English translation).
(Continued)

*Primary Examiner* — Michael A Berns
(74) *Attorney, Agent, or Firm* — Fish & Richardson P.C.

(57) ABSTRACT

Provided are a system and a method for providing service to recommend customized exercise used for autonomous vehicle. The system and method are configured to determine whether the user does the exercise safely and freely during autonomous control of the vehicle through the monitoring system in the autonomous vehicle and recommend the customized exercise used for the autonomous vehicle according to a situation of the user and the situation of the autonomous control and to determine whether the user does the exercise safely and freely during the autonomous control of the vehicle through the monitoring system in the autonomous vehicle and recommend the autonomous vehicle in which the user can do the recommended exercise according to the situation of the user and the situation of the autonomous control.

14 Claims, 5 Drawing Sheets

1

(51) Int. Cl.
*G16H 40/67* (2018.01)
*G16H 50/20* (2018.01)
*B60W 40/04* (2006.01)
*B60W 50/14* (2020.01)
*G01S 19/14* (2010.01)
*G06Q 10/06* (2012.01)
*G06Q 50/26* (2012.01)
*G06Q 50/30* (2012.01)
*G08G 1/01* (2006.01)

(52) U.S. Cl.
CPC ........ *G01S 19/14* (2013.01); *G06Q 10/06315* (2013.01); *G06Q 50/26* (2013.01); *G06Q 50/30* (2013.01); *G08G 1/0108* (2013.01); *G08G 1/0125* (2013.01); *G08G 1/0137* (2013.01); *G16H 20/30* (2018.01); *G16H 40/67* (2018.01); *G16H 50/20* (2018.01); *B60W 60/0016* (2020.02); *B60W 2050/146* (2013.01); *B60W 2556/50* (2020.02)

(56) References Cited

U.S. PATENT DOCUMENTS

| | | | | |
|---|---|---|---|---|
| 9,801,134 | B2* | 10/2017 | Hwang | H04W 56/0045 |
| 10,882,530 | B2* | 1/2021 | Kumazaki | B60W 50/0098 |
| 2015/0182160 | A1* | 7/2015 | Kim | A61B 5/742 |
| | | | | 600/301 |
| 2018/0008855 | A1* | 1/2018 | Yanev | A63B 24/0062 |
| 2019/0039622 | A1 | 2/2019 | Kumazaki | |

FOREIGN PATENT DOCUMENTS

| | | |
|---|---|---|
| KR | 20130025510 | 3/2013 |
| KR | 20130117402 | 10/2013 |
| KR | 101740529 | 5/2017 |
| KR | 20180051867 | 5/2018 |

OTHER PUBLICATIONS

Lee, "Hyundai Motors, "Exercise with a rowing machine in a car in the era of autonomous driving,"." Dated Jan. 9, 2019, Biz New Daily Korea, 3 pages (with English translation).

Korean Office Action in Korean Appln. No. 10-2019-7019622, dated Oct. 15, 2020, 15 pages (with English translation).

Ministry of Land, Infrastructure and Transport and Korea Agency for Infrastructure Technology Advancement, "Final report on self-driving-based car sharing service test operation research," SK Telecom, dated Feb. 10, 2019, 121 pages (with English summary).

* cited by examiner

SYSTEM AND METHOD FOR PROVIDING CUSTOMIZED RECOMMENDATION SERVICE USED FOR AUTONOMOUS VEHICLE

CROSS-REFERENCE TO RELATED APPLICATIONS

This application is a National Stage application under 35 U.S.C. § 371 of International Application No. PCT/KR2019/002760, filed on Mar. 8, 2019, the contents of which are hereby incorporated by reference herein in their entirety.

TECHNICAL FIELD

An autonomous vehicle that determines whether a user does an exercise safely and freely during autonomous control of the vehicle, through a monitoring system in the autonomous vehicle, and may recommended exercise according to a situation of the user and a situation of autonomous control, and a system and a method of providing service to recommend customized exercise used for the autonomous vehicle.

BACKGROUND ART

In recent years, technology has been developed for an autonomous vehicle that autonomously operates to a destination thereof by itself without an operation of a driver.

With the development of autonomous vehicles, a space within the vehicle may function as an independent space where a user may live and perform activities, rather than a space to move the user only.

Accordingly, passengers may perform a variety of activities during movement of the autonomous vehicle, and various kinds of services may be expected to be one of future industries for passengers who may move freely in the vehicle, as customers.

In recent years, U-health services that utilize IT for exercise prescription are being studied. The U-health service may refer to providing exercise recommendation services to people anytime and anywhere using a system that connects various types of exercise apparatuses and apparatuses of measuring health information to computers.

In order to provide the exercise recommendation service in the U-health environment, it is required that previously constructed contents may cope with all situations during the exercise service. The exercise recommendation service may require a system that manages all processes for recommendation and exercise prescription through systematized knowledge.

In order to effectively cope with such an exceptional situation, the situation that may occur during the exercise and an appropriate response to the situation are very important. However, research on contents with respect to the information on situation to recommend exercise, which is currently being made, may be limited to a case in which the exercise is performed in a fixed and stable space, such as a health club. That is, the research is being studied to do an efficient exercise only in consideration of a state of a user (a health state, a body condition, disease, and the like) and an amount of exercise simply, by providing a method of using various types of exercise apparatuses, which may be used in a space in which various types of exercise apparatuses are installed (health clubs, home, and the like) or the road for running, and a method of exercising.

However, in order to provide the passenger with the exercise recommendation service in the U-health environment during movement of the autonomous vehicle, it may be required to recommend the exercise according to the situation of the autonomous control in consideration of dangerous elements that may occur according to the movement of the vehicle during the exercise.

Accordingly, it may be required to consider various kinds of events and information on the situation according to the movement of the vehicle to provide the passenger with the exercise recommendation service in the U-health environment to the passenger during the movement of the autonomous vehicle. In other words, there is a need for intuitive service in the U-health environment customized according to the situation of the user and the situation of the autonomous control by determining whether the user does the exercise safely and freely using a computing technology based on situation recognition.

DISCLOSURE

Technical Problem

The present disclosure relates to a system and a method of providing service to recommend customized exercise that is used for an autonomous vehicle according to a situation of a user and a situation of autonomous control by determining whether the user does the exercise safely and freely during autonomous control of the vehicle, through a monitoring system in the autonomous vehicle.

The present disclosure relates to an apparatus and a method of providing service to recommend an autonomous vehicle in which the user may do the recommended exercise according to the situation of the user and the situation of the autonomous control by determining whether the user does the exercise safely and freely during the autonomous control of the vehicle through the monitoring system in the vehicle.

The present disclosure provides an apparatus and a method of providing service to recommend customized exercise used for an autonomous vehicle that determines whether the user does the exercise safely and freely during the autonomous control of the vehicle through the monitoring system in the autonomous vehicle.

The present disclosure provides an apparatus and a method of providing service to recommend customized exercise that may utilize evaluation service with respect to danger and a degree of freedom of exercise by collecting information whether the user does the exercise safely and freely during the autonomous control of the vehicle.

The objects of the present disclosure are not limited to the above-mentioned objects, and other objects and advantages of the present disclosure which are not mentioned can be understood by the following description and more clearly understood by the embodiments of the present disclosure. It will also be readily apparent that the objects and advantages of the present disclosure can be implemented by features defied in claims and a combination thereof.

Technical Solution

According to the present disclosure, a customized recommendation service providing system may include a server that selects an autonomous vehicle in which a user may do a customized recommendation exercise according to a situation of users and a situation of autonomous control and transmits information on a route of the autonomous vehicle to the selected autonomous vehicle, to allocate the autonomous vehicle to a user terminal, and it is possible to recommend the autonomous vehicle in which the user may do the recommended exercise according to the situation of users and the situation of the autonomous control.

According to the present disclosure, a customized recommendation service providing system may include a server that generates customized exercise schedule according to the situation of the users and the situation of autonomous control and provides an autonomous vehicle arrived at an arrival place with the generated customized exercise schedule, and it is possible to recommend the customized exercise used for the autonomous vehicle according to the situation of the user and the situation of the autonomous control.

The present disclosure may provide an autonomous vehicle that recommends a customized exercise in a U-health environment according to the situation of the user and the situation of the autonomous control during the autonomous control of the vehicle based on the customized exercise schedule through a monitoring system in the vehicle.

According to the present disclosure, the server may include an exercise schedule management that generates a customized exercise schedule by selecting the desired exercise in consideration of a travel route and a traffic situation detected based on the information on a position of the user and the arrival place so that the user may use an exercise apparatus suitable for the user conveniently and efficiently.

According to the present disclosure, the server may include the vehicle allocation management that detects the vehicle based on the information on the position of the vehicle and stabilizer for each vehicle through location tracking service and may prevent dangerous elements that may occur according to the movement of the vehicle moves during exercise, to provide a safe method of using an exercise apparatus and a method of exercising.

According to the present disclosure, the server may include a situation monitoring unit that detects information on collected dynamic situation and checks a period of time for which a dynamic situation occurs and an exercise set performed while the dynamic situation occurs according to the customized exercise schedule; a situation management that receives the information on the dynamic situation identified by the situation monitoring unit and detects an exercise set having an exercise effect similar to that of an exercise set determined to be in a dangerous situation with reference to a previously stored situation learning model; and an exercise schedule corrector that replaces the exercise set detected by the situation management with a corresponding exercise set, among exercise sets included in the customized exercise schedule and corrects the customized exercise schedule, to prevent even the dangerous elements that may occur due to the movement of the vehicle during exercise.

Advantageous Effects

According to the present disclosure, it may determine whether a user does an exercise safely and freely during autonomous control of a vehicle through a monitoring system in an autonomous vehicle to suitably cope with a situation of a user and a situation of autonomous control, thereby improving reliability with respect to service to recommend exercise during the autonomous control.

According to the present disclosure, it is possible to determine whether the user does the exercise safely and freely during the autonomous control of the vehicle through the monitoring system in the vehicle and to recommend the autonomous vehicle in which the user may do the recommended exercise according to the situation of the user and the situation of the autonomous driving, thereby conveniently and effectively an exercise apparatus suitable for the user.

According to the present disclosure, it is possible to determine whether the user does the exercise safely and feely during the autonomous control of the vehicle through the monitoring system in the autonomous vehicle and prevent even the dangerous elements that may occur according to the movement of the vehicle during the exercise, thereby providing a safe method of using the exercise apparatus and a safe method of exercise.

According to the present disclosure, information whether the user does the exercise safely and freely during the autonomous control of the vehicle is collected to use the evaluation service with respect to the danger and the degree of freedom of exercise.

The present disclosure may provide the customized recommendation service used for the autonomous vehicle, thereby improving satisfaction of the user.

Specific effects of the present disclosure, in addition to the above-mentioned effect, will be described together while describing a specific matter to implement the present disclosure.

BEST MODE

Figure 1:
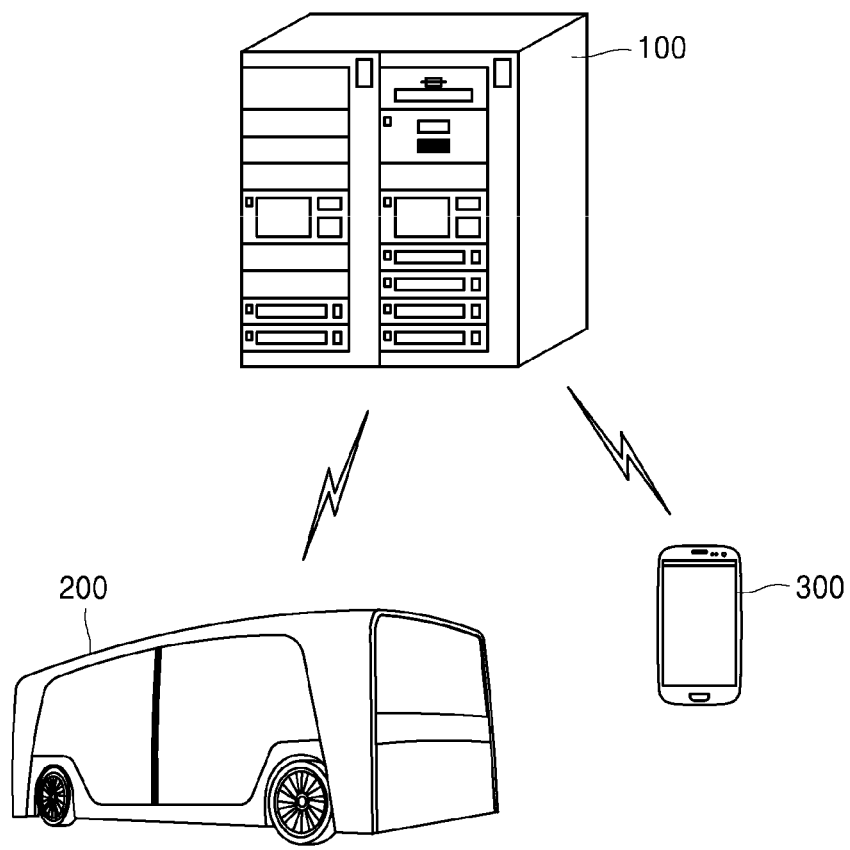
FIG. 1 is a configuration diagram of a configuration of an overall system for a customized recommendation service used for an autonomous vehicle according to an embodiment of the present disclosure.

The above objects, features, and advantages will be described in detail with reference to the accompanying drawings, and accordingly, the skilled person in the art to which the present disclosure pertains may easily implement the technical idea of the present disclosure. Further, in describing the present disclosure, a detailed description of known configurations related to the present disclosure will be omitted when it is determined that it may obscure the gist of the present disclosure. Preferred embodiments of the present disclosure will be described in detail below with reference to the accompanying drawings. In the drawings, same reference numerals are used to indicate same or similar components.

When a component is described as being "connected", "coupled", or "connected" to another component, the component may be directly connected or able to be connected to the other component; however, it is also to be understood that an additional component may be "interposed" between the two components, or the two components may be "connected", "coupled" or "connected" through an additional component.

The present disclosure relates to a system and a method of providing a customized recommendation service used for an autonomous vehicle. Hereinafter, an apparatus and a method of providing customized recommendation service used for the autonomous vehicle according to an embodiment of the present disclosure will be described in detail with reference to FIGS. 1 to 5.

FIG. 1 is a configuration diagram of a configuration of an overall system for customized recommendation service used for an autonomous vehicle according to an embodiment of the present disclosure.

As shown in FIG. 1, according to the present disclosure, a customized recommendation service providing system 1 may include a server 100, an autonomous vehicle 200, and a user terminal 300. An embodiment is the customized recommendation service providing system 1 shown in FIG. 1 and that component is not limited to the embodiment shown in FIG. 1. Some components may be added, changed, or deleted as necessary.

The server 100, the autonomous vehicle 200, and the user terminal 300 included in the customized recommendation service providing system 1 may be connected to one another through a wireless network, to perform mutual data communication.

In the present disclosure, the user terminal 300 may be defined as a terminal of a user who is provided with customized recommendation service. That is, the user terminal 300 may be provided as one of various types of components, for example, electronic apparatus such as a computer, a Ultra Mobile PC (UMPC), a workstation, a net-book, a Personal Digital Assistants (PDA), a portable computer, a web tablet, a wireless phone, a mobile phone, a smart phone, an e-book, a portable multimedia player (PMP), a portable game machine, a navigation apparatus, a black box or a digital camera, which are related to the autonomous vehicle 200 and are carried by user. However, the present disclosure is not limited thereto.

In order for the user terminal 300 to receive the customized recommendation service, an application for customized recommendation service may be installed in the user terminal 300. The user terminal 300 is driven by the operation of the user and the user executes the installed application through a simple method in which the user selects (touches or presses buttons) for customized recommendation service displayed on a display window (a screen) of the user terminal 300 to access the server 100.

Further, information on the position itself provided by a GPS satellite and geographical information to be displayed on the map, for example, geographical information provided by the GIS may be stored in and managed by the user terminal 300. That is, the user terminal 300 may display information on the position itself and the position of the autonomous vehicle 200 in real time through a method in which the user terminal 300 receives the information on the position of the autonomous vehicle 200 (for example, position coordinates) in a data form and it displays it on the map stored in the terminal.

The server 100 selects an autonomous vehicle, where the user may do a customized recommendation exercise in the autonomous vehicle, according to the situation of the user and the situation of the autonomous control. At this time, the autonomous vehicle 200 is selected based on the GPS information of the user terminal 300, according to the position of the user, the arrival place, and whether the exercise apparatus through which the user may do the desired exercise, is provided. The server 100 transmits information on the route of the autonomous vehicle to the selected autonomous vehicle and allocates the autonomous vehicle to the user. At this time, the server 100 may allow the autonomous vehicle to arrive at the position of the user through the autonomous control.

At this time, the server 100 may identify a current position of the autonomous vehicle 200 through a GPS signal received from a GPS module of the autonomous vehicle 200. Further, the server 100 may refer to database or access traffic information server to identify an arrival position corresponding to the information on the arrival position. Based on the above, the server 100 may generate a route of the autonomous vehicle that is currently moving from the position of the autonomous vehicle 200 to the arrival position.

The server 100 may generate a customized exercise schedule according to the situation of the user and the situation of the autonomous control, and may provide the generated customized exercise schedule to the autonomous vehicle 200 that arrives at the arrival place. At this time, the situation of the user may include information on a physical strength including age, health state, body information, disease or not, exercise preference, and the like, and environmental information including a type of exercise apparatus, exercise intensity, exercise time, a current state, and the like. Further, the situation of the autonomous control may include dynamic information including a road situation, a traffic situation, from the position of the user to the arrival place, a possible arrival time, a vehicle speed, and the like.

At this time, information on physiology signal measured by pressure device, a pulse measuring device, through the user terminal 300, information input to the user terminal 300 in real time, or previously stored information, in which information input through an existing membership is stored may be used as the information on the physical strength and the environmental information. The server 100 has a feature of generating the customized exercise schedule based on the input information on the physical strength of the user, and a method of receiving the information on the physical strength is not limited thereto and may receive the information on the physical strength through various known embodiments.

To this end, the server 100 has a hardware having the same configuration as a general web-server and has software including a program module that is implemented through various types of languages, for example, C, C++, Java, Visual Basic, Visual C, and the like and performs various types of functions. The server 100 may be constructed based on cloud and may store and manage information collected by the autonomous vehicle 200 and the user terminal 300 connected to each other through the wireless network. The server 100 may be operated by a transportation enterprise server such as a car-sharing company and may control the autonomous vehicle 200 using wireless data communication.

The server 100 may access to any transportation enterprise server (not shown) and call the transportation enterprise vehicle movable to the position corresponding to the information on the arrival position, to the position of the autonomous vehicle 200. Transportation enterprise server may manage the operation of any transportation enterprise vehicle. For example, the server may be a server of a taxi company that manages operation of a manned taxi or an unmanned taxi (autonomous taxi).

The server 100 may identify the current position of the autonomous vehicle 200 based on the GPS signal received from the GPS module of the autonomous vehicle 200. The server 100 may transmit information on the current position of the identified autonomous vehicle 200 as a departure point to the transportation enterprise server and transmit information on the arrival position corresponding to the information on the arrival position as a destination to the transportation enterprise server to call the transportation enterprise vehicle.

The transportation enterprise server may search for a transportation enterprise vehicle that may be moved from the current position to the arrival position, of the autonomous vehicle 200, and may drive the vehicle to the current position of the autonomous vehicle 200. For example, when the taxi managed by the transportation enterprise server is a manned taxi, the transportation server may provide the driver of the taxi with information on the current position of the autonomous vehicle 200. To the contrary, when the taxi managed by the transportation enterprise server is an unmanned taxi, the transportation enterprise server generates a route of the autonomous vehicle from the current position of the taxi to the current position of the autonomous vehicle 200 and may control for the taxi to operate along the route of the autonomous vehicle.

The detailed configuration of the server 100 will be described below with reference to FIG. 2.

The autonomous vehicle 200 determines whether the user does the exercise safely and freely during autonomous control of the vehicle based on the customized exercise schedule through a monitoring system in the vehicle to recommend the customized exercise in the U-health environment according to the situation of the user and the situation of the autonomous control. The autonomous vehicle 200 may include an exercise apparatus through which the user may do the customized recommendation exercise, and may be operated by the transportation enterprise server of a car-sharing company which provides a reservation for the vehicle and renting of the vehicle.

At this time, the autonomous vehicle 200 travels to a destination by itself without the operation of the operator. The autonomous vehicle 200 may have a concept including any moving means such as automobiles and motorcycles; however, it is described that the autonomous vehicle 200 is an automobile for convenience of explanation.

The detailed configuration of the autonomous vehicle 200 will be described below with reference to FIGS. 3 and 4.

Figure 2:
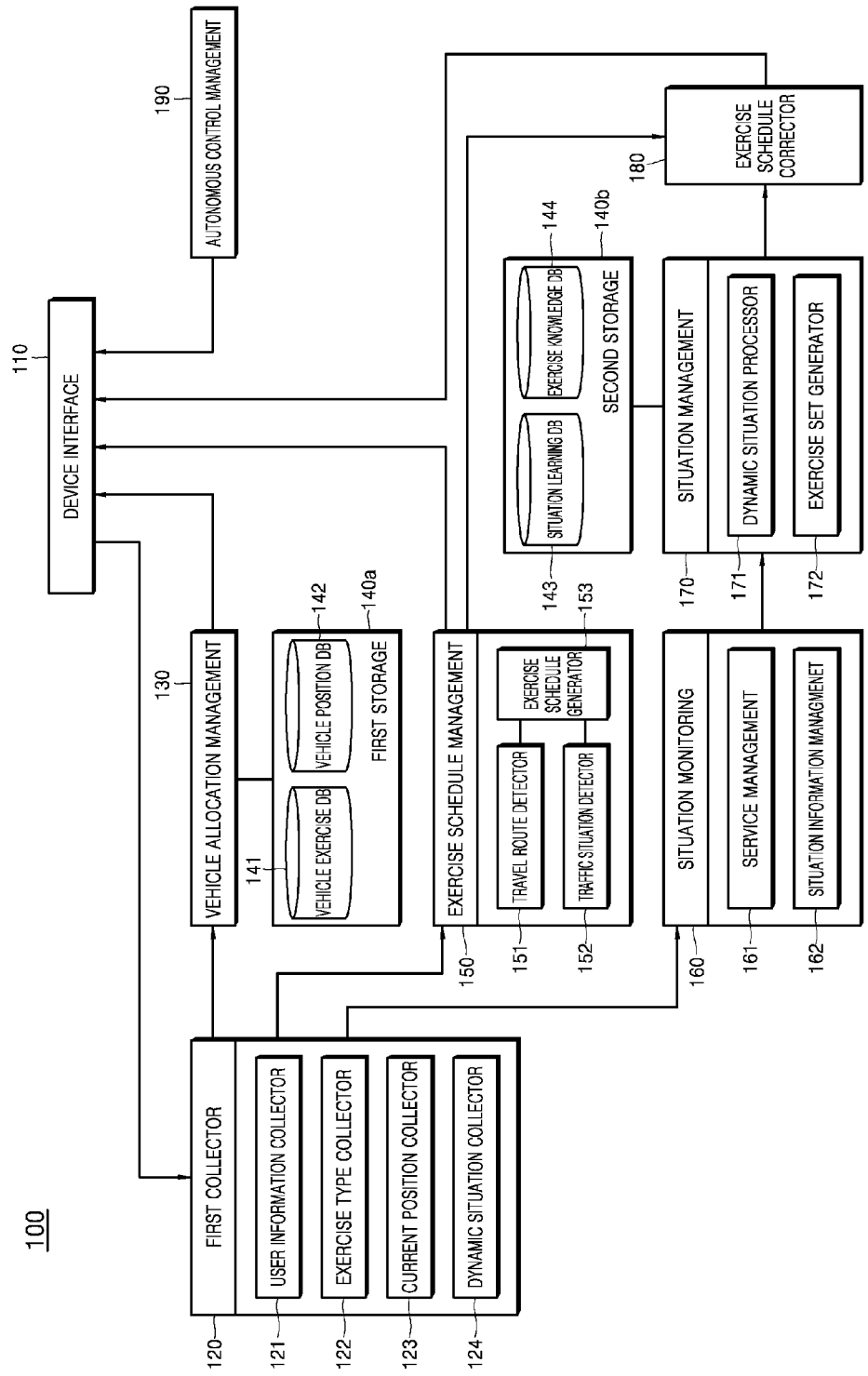
FIG. 2 is a configuration diagram of the autonomous vehicle shown in FIG. 1.

FIG. 2 is a block diagram of a detailed configuration of the server shown in FIG. 1.

As shown in FIG. 2, a server 100 includes a device interface 110, a first collector 120, a vehicle allocation management 130, first and second storages 140a and 140b, an exercise schedule management 150, a situation monitoring unit 160, a situation management 170, and an exercise schedule corrector 180. The server 100 further includes an autonomous control management 190.

As the present disclosure is a disclosure that provides a customized recommendation service used for the autonomous vehicle, rather than a disclosure related to the autonomous control of the vehicle, details of the autonomous control management 190 will be omitted. The autonomous control management 190 is a module to control for the vehicle to be autonomously controlled and may be implemented using a currently known technology of autonomous control.

The device interface 110 of the server 100 is provided among an autonomous vehicle 200, a user terminal 300, and the server 100 and transmits and receives input/output data through a wired and wireless network.

The first collector 120 of the server 100 collects user information, information on desired exercise from the autonomous vehicle 200 and the user terminal 300 and collects current positions and dynamic situation from the autonomous vehicle 200 and the user terminal 300, through the device interface 110. To this end, the first collector 120 includes a user information collector 121, an exercise type collector 122, a current position collector 123, and a dynamic situation collector 124.

The user information collector 121 of the first collector 120 collects user information transmitted by the user terminal 300. The user information may be information on a physical strength including age, health state, body information, disease or not, a current state, and the like. At this time, information on a physiology signal measured by a blood pressure device, and the pulse measuring device, and the like, through the user terminal 300, information input to the user terminal 300 in real time, or previously stored information on input through the existing membership may be used as the information on the physical strength.

The exercise type collector 122 of the first collector 120 collects information on desired exercise transmitted by the user terminal 300. The information on the desired exercise may be environmental information including a type of exercise apparatus, exercise intensity, exercise time, and the like. At this time, driving information of the exercise apparatus 220 which is currently used based on the exercise schedule, information input to the user terminal 300 in real time, or previously stored information in which input information is stored through the existing membership may be used as the environmental information.

The current position collector 123 of the first collector 120 collects information on the current positions of the vehicle which is autonomously controlling and the user terminal 300. The information on the current position may include information on the current position provided by the GPS satellite via the GPS module attached to the autonomous vehicle 200 and the user terminal 300 and geographical information to be displayed on the map.

The dynamic situation collector 124 of the first collector 120 may collect the situation on the autonomous control including dynamic information including a road situation, a traffic situation, a possible arrival time, a vehicle speed a dangerous situation, and the like, which are detected during travelling from the position of the user to the arrival place.

The vehicle allocation management 130 of the server 100 detects the autonomous vehicle for exercise that may service the desired exercised based on at least one of the user information, the information on the desired exercise, information on the current position and the dynamic situation collected by the first collector 120 and allocate the autonomous vehicle to the user.

To this end, the vehicle allocation management 130 detects the vehicle based on the information on the position of the vehicle and the information on the stabilizer for each vehicle through location tracking service such as geofencing. That is, a level of stability of a stabilizer, and the like, of the vehicle for exercising detected in a predetermined area is determined based on the type of exercise desired by the user, to detect the possible vehicle. To this end, the first storage unit 140a previously stores information on the position of the vehicle and the information on the stabilizer for each vehicle. Meanwhile, the level of the stabilizer may be determined in advance by dividing the level of the stabilizer into a range of acceleration in which the vehicle may be balanced, a slope of the vehicle, and a reaction speed for a specific event when the user does the exercise during the autonomous control. Further, the level of the stabilizer is determined based on the desired exercise. For example, the level of the stabilizer is low in the case of yoga, and the level of the stabilizer is normal in case of cyber soccer, and the level of the stabilizer is high in the case of bodybuilding. As described above, the vehicle allocation management 130 may set the level of the stabilizer in advance for each type of exercise.

Further, the vehicle allocation management 130 provides the user terminal 300 with the detected vehicle list and information on the possible arrival time (or the parked road). The vehicle allocation management 130 allocates the vehicle selected (determined) by the user, in the provided vehicle list, and transmits the information on the position of the user to the autonomous vehicle 200 by the autonomous control management 190 so that the autonomous control 200 may reach the position of the user through autonomous control. At this time, an embodiment is travelling of the autonomous vehicle 200, but is not limited thereto. For example, the information on the position at which the autonomous vehicle 200 is parked, to the user terminal 300, the user may directly move the position at which the autonomous vehicle 200 is parked.

The first and second storage units 140*a* in the server 100 store information on the current position of the vehicle, in which the autonomous vehicles 200 are parked, and information on a level of the stabilizer set for each vehicle. The first and second storage units 140*a* stores the information on the current position of the vehicle and the information on a level of the stabilizer, in a vehicle position DB 142 and a movement DB 141, respectively.

The exercise schedule management 150 in the server 100 selects a desired exercise in consideration of the travel route and the traffic situation detected based on the information on the position of the user and the arrival place collected by the first collector 120 and generates the exercise schedule. To this end, the exercise schedule management 150 includes a travel route detector 151, a traffic situation detector 152, and an exercise schedule generator 153.

The travel route detector 151 in the exercise schedule management 150 detects the travel route based on the position of the user and the arrival place. At this time, the travel route is detected based on at least one of an optimal time, an optimal distance, toll-free service, and route recommendation, from the departure point to the destination.

The traffic situation detector 152 of the exercise schedule management 150 detects the current traffic situations in real time for each travel route detected by the traveling path detector 151. At this time, a real-time traffic situation may be used by collecting the traffic information provided, by the traffic center of the Korea Expressway Corporation, in real time.

The exercise schedule generator 153 of the exercise schedule management 150 analyzes the type of exercise of the exercise apparatus 220 placed in the allocated autonomous vehicle 200, based on the desired exercise, and generate one or more candidate exercise schedules based on the information on the user and the environmental information. The exercise schedule generator 153 analyzes a road complexity, a speed of the autonomous vehicle for each section, and a travelling time of the autonomous vehicle for each section, and the like, based on the travel route and the traffic situation detected by the travel route detector 151 and the traffic situation detector 152, and determine the exercise set in combination with the types of exercises that may be performed for each section. The exercise schedule generator 153 generates a customized exercise schedule by matching the determined types of exercise sets and the methods of exercise, among the generated candidate exercise schedules, over time.

The situation monitoring unit 160 of the server 100 detects the dynamic state collected by the first collector 120 and checks a period of time for which the dynamic situation occurs and the exercise set performed while the dynamic situation occurs according to the generated exercise schedule. At this time, the dynamic situation may include a road situation, a traffic situation, a possible arrival time, a vehicle speed, a dangerous situation, and the like, which are detected during traveling from the position of the user to the arrival place. To this end, the situation monitoring unit 160 includes a service management 161 and a situation information management 162.

The service management 161 of the situation monitoring unit 160 receives the information on the collected dynamic situation and converts the exercise schedule into an environment to provide the service, and provides the user with the service through the user terminal.

The situation information management 162 of the situation monitoring unit 160 checks the period of time for which the dynamic situation occurs and the exercise set performed while the dynamic situation occurs according to the exercise schedule based on the detected dynamic situation.

The situation management 170 of the server 100 receives the information on the dynamic situation (the period of time for which the dynamic situation occurs and the exercise set performed while the dynamic situation occurs) identified by the situation monitoring unit 160 and detects the exercise set having an exercise effect similar to that of the exercise set determined to be in the dangerous situation with reference to the previously stored situation learning model. To this end, the situation management 170 includes a dynamic situation processor 170 and an exercise set generator 172.

The dynamic situation processor 171 of the situation management 170 receives the information on the dynamic situation (the period of time for which the dynamic situation occurs and the exercise set performed while the dynamic situation occurs) identified by the situation monitoring unit 160, and determines the dangerous situation among exercise sets included in the customized exercise schedule generated by the exercise schedule management 150 with reference to the previously stored situation learning model.

For example, when the traveling vehicle is greatly shaken, the exercise during performing according to the exercise schedule may be in the dangerous situation, that is, a case in which the user performs the exercise using running machine or using heavy equipment such as a barbell may be determined as a case in which the dangerous situation occurs. To the contrary, even when the vehicle is greatly shaken, the case in which the user performs the exercise using cycle may not be determined to be in the dangerous situation. However, it is merely one embodiment, but is not limited thereto.

As described above, the server 100 may correspond the exercise schedule to the dynamic situations that may occur for each type of exercise and previously set whether the dangerous situation occurs, and generate the situation learning model, to previously store the generated situation learning model to the situation learning DB 143 of the second storage 140*b*.

The exercise set generator 172 of the situation management 170 checks the exercise set corresponding to the dangerous situation determined by the dynamic situation processor 171 and detects an exercise set having an exercise effect similar to that of the determined exercise set based on the previously stored information on exercise knowledge.

The server 100 may previously set the exercise set having the similar exercise effect, including the type of exercise apparatus, exercise intensity, exercise time, and the like for each dynamic situation, and previously store it in the exercise knowledge DB 144 of the second storage 140b in advance.

The exercise schedule corrector 180 of the server 100 replaces the exercise set detected by the situation management 170 with the corresponding exercise set, among exercise sets included in the customized exercise schedule generated by the exercise schedule management 150, to correct the customized exercise schedule. At this time, the exercise schedule corrector 180 may continually change the customized exercise schedule to the corrected customized exercise schedule until the autonomous vehicle 200 arrives at the arrival position.

Figure 3:
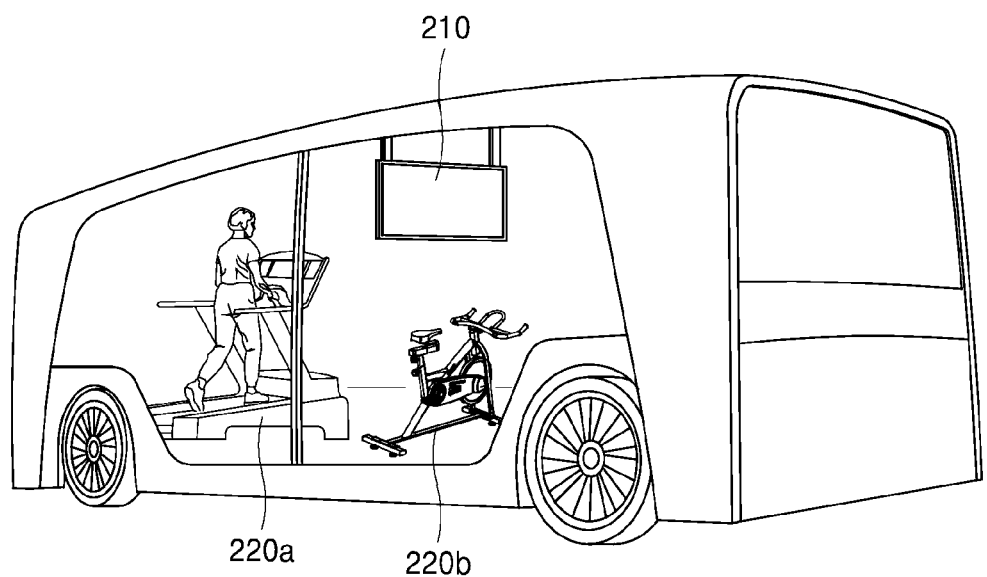
FIG. 3 is a block diagram of a detailed configuration of the autonomous vehicle shown in FIG. 1.
Figure 4:
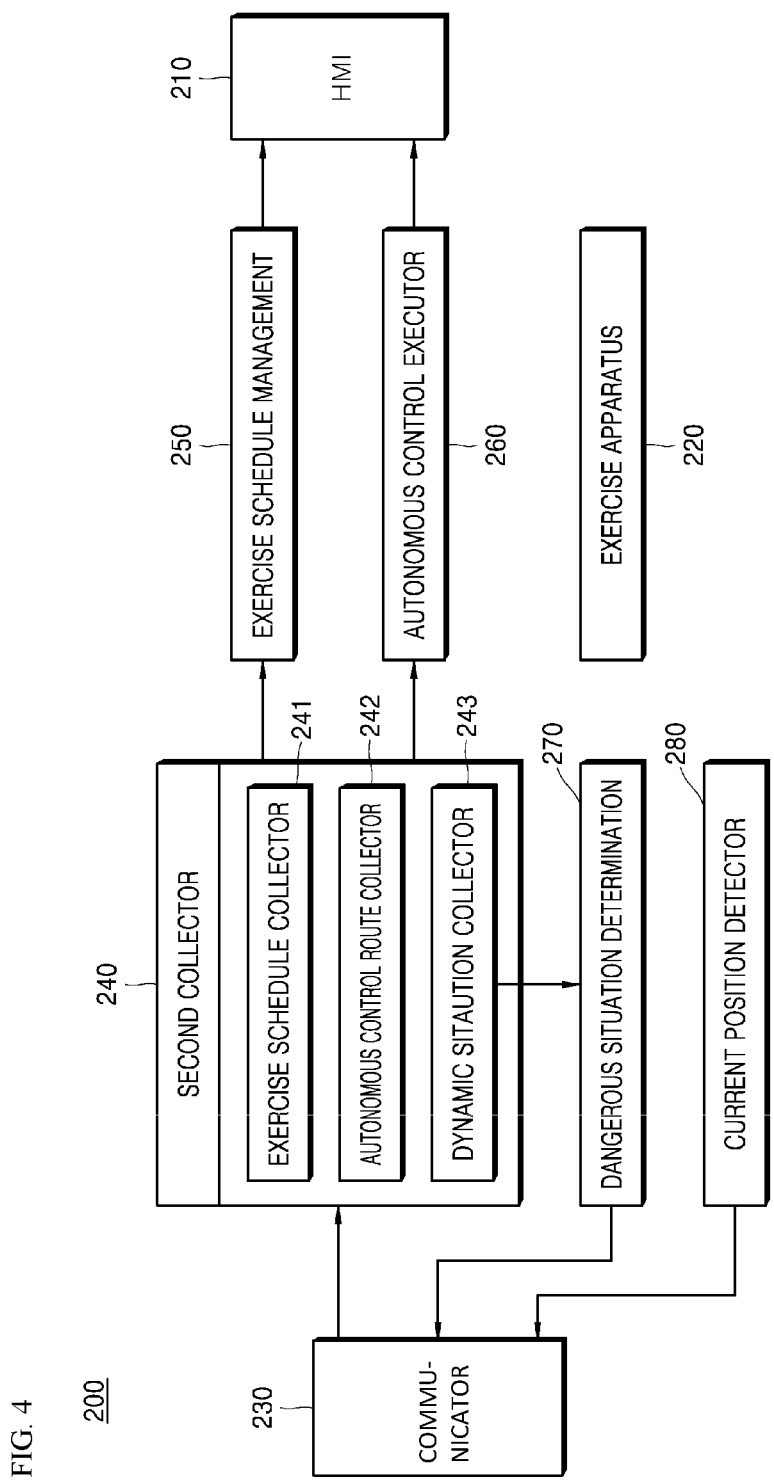
FIG. 4 is a block diagram of a detailed configuration of the server shown in FIG. 1.

FIG. 3 is a configuration diagram of the autonomous vehicle shown in FIG. 1, and FIG. 4 is a block diagram of a detailed configuration of the autonomous vehicle shown in FIG. 1.

As shown in FIGS. 3 and 4, an autonomous vehicle 200 may include a Human Machine Interface (HMI) 210 and at least one exercise apparatus 220. Further, the autonomous vehicle 200 may include a communicator 230, a second collector 240, an exercise schedule management 250, an autonomous control executor 260, a dangerous situation determination 270, and a current position detector 280.

The HMI 210 of the autonomous vehicle 200 may perform a function for visually and audibly outputting information or a state of the vehicle through a physical interface and provide the output information or state of the vehicle to the driver. Further, during provision of the customized exercise recommendation service during the autonomous control, the HMI 210 may receive the user operation to provide the customized exercise recommendation service, or output the information related to the customized exercise (the type of the exercise apparatus, the exercise posture, notification, an exercise time, and the like), or output danger notifications. In addition, the HMI 210 may perform a function for controlling the autonomous control of the autonomous vehicle 200.

The exercise apparatus 220 of the autonomous vehicle 200 is configured for the user to do a desired exercise in the vehicle during autonomous control, and is fixed into and installed inside of the autonomous vehicle 200. For example, the exercise apparatus 220 may include a running machine, a health bicycle, a squad, a balance power, a chinning dipping bar, a weight apparatus, and the like.

The communicator 230 of the autonomous vehicle 200 may transmit and receive input/output data among the server 100 and the user terminal 300 and the autonomous vehicle 200 using a wired or wireless communication network. At this time, the communication network connects the server 100, the autonomous vehicle 200, and the user terminal 300, and may include a repeater, and may include a mobile communication network (3G network, 4G network, WiBro network) installed and operated by communication corporations, and Internet network/Public Switched Telephone Network (PSTN). The repeater may include a base station or an access point (AP).

The second collector 240 of the autonomous vehicle 200 collects information on the customized exercise schedule, routes of the autonomous vehicle, and dynamic situations transmitted by the server 100 through the communicator 230. At this time, the dynamic situation may include information on road complexity, speed for each section, and travel time for each section based on the detected travel route and traffic situation transmitted by the server 100. However, the present disclosure is not limited thereto. That is, the dynamic situation may include an unexpected situation such as a user emergency situation or a rod emergency situation occurring during travelling of the autonomous vehicle 200, and the unexpected situation may be input from the user terminal 300 and the autonomous vehicle 200.

To this end, the second collector 240 includes an exercise schedule collector 241, an autonomous travel route collector 242, and a dynamic situation collector 243.

The exercise schedule collector 241 of the second collector 240 may collect customized exercise schedules transmitted by the server 100. After the exercise schedule collector 241 collects the customized exercise schedule, when the corrected customized exercise schedule is input from the server 100, it is possible to change the collected customized exercise schedule to the corrected customized exercise schedule which is input afterwards. That is, the exercise schedule collector 241 may change a current customized exercise schedule to the customized exercise schedule, which is input later, anyway.

The autonomous travel route collector 242 of the second collector 240 may collect the route of the autonomous vehicle transmitted by the server 100. At this time, the route of the autonomous vehicle is generated with reference to traffic information from the current position of the autonomous vehicle 200 to the arrival position.

The dynamic situation collector 243 of the second collector 240 collects dynamic situations such as an unexpected situation, for example, a user emergency situation or a road emergency situation occurring during the travelling of the autonomous vehicle 200. For example, the unexpected situation of the user emergency situation may include injuries, respiratory difficulty, collapse, and the like during exercise. In this case, the user may select an emergency button installed around the user terminal 300 or the exercise apparatus 220 to request for notification of the emergency situation. Further, the unexpected situation of the road emergency situation may include a situation of brakes due to collision accidents, and obstacles.

The exercise schedule management 250 of the autonomous vehicle 200 provides the customized exercise schedule collected by the second collector 240 to the HMI 210. The exercise schedule management 250 transmits timing information to adjust a term of exercise according to a route of the autonomous vehicle through exercise scheduling provided by the HMI 210. For example, when safety is maintained, exercise is recommended, and when there is a dangerous element, it is recommended to relax.

The autonomous control executor 260 of the autonomous vehicle 200 executes the autonomous control of the autonomous vehicle along the route of the autonomous vehicle collected by the second collector 240. At this time, as the present disclosure is an invention that provides a customized recommendation service to be used for the autonomous vehicle, rather than an invention related to the autonomous control of the vehicle, details thereof to perform the autonomous control of the vehicle, by the autonomous control executor 260, is omitted. However, the autonomous control executor 260 may use a control signal so that the vehicle autonomously travels, by the autonomous executor 190, and it may be implemented using a presently known autonomous control technology.

The danger situation determination 270 of the autonomous vehicle 200 receives the information on the dynamic situation collected by the second collector 240 and transmits the information on the dynamic situation to the server 100 through the communicator 230 in real time. At this time, the received information on the dynamic situation may be a dynamic situation such as an unexpected situation, for example, a user emergency situation or a road emergency situation occurring during travelling of the autonomous vehicle 200.

The current position detector 280 of the autonomous vehicle 200 detects the current position provided by the GPS satellites via the GPS module attached to the autonomous vehicle. The current position detector 280 may display the detected current position on the map provided by the HMI 210 in real time. Further, the current position detector 280 transmits information on the detected current position to the server 100 through the communicator 230 in real time.

Hereinafter, operation of the system of providing the customized recommendation service used for the autonomous vehicle according to the present disclosure will be described in detail with reference to the accompanying drawings. Reference numerals same as FIGS. 1 to 4 refer to same elements that perform the same function.

Figure 5:
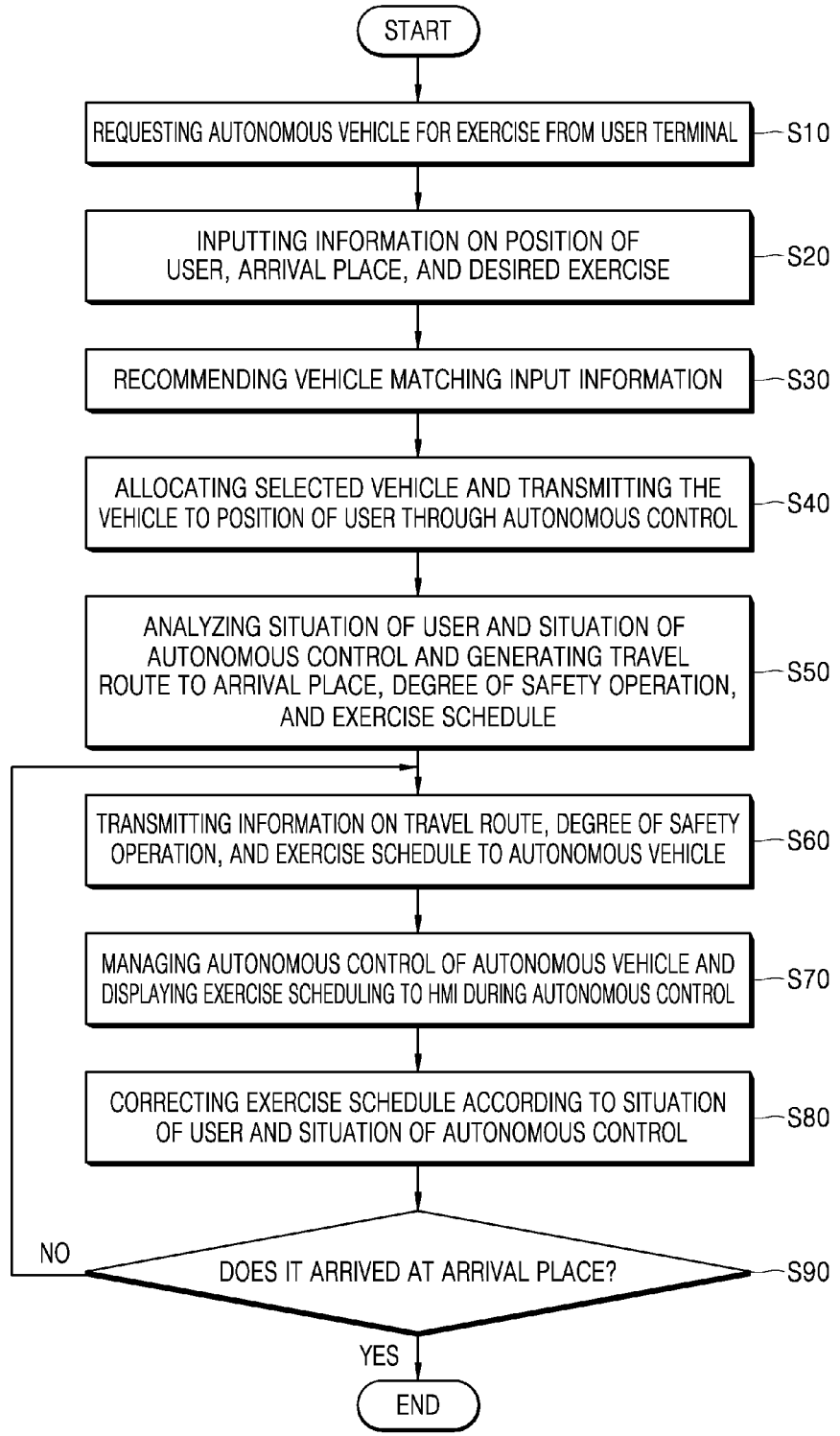
FIG. 5 is a flowchart of a method for providing a customized recommendation service used for an autonomous vehicle according to an embodiment of the present disclosure.

FIG. 5 is a flowchart of a method for providing a customized recommendation service used for an autonomous vehicle according to an embodiment of the present disclosure.

Referring to FIG. 5, in a server 100, when a request for an autonomous vehicle for exercise is transmitted from a user terminal (S10), a first collector 120 collects user information and information on desired exercise from an autonomous vehicle 200 and the user terminal 300, and collects current positions and dynamic situations of the autonomous vehicle 200 and the user terminal 300.

At this time, an application for a customized recommendation service may be installed in the user terminal 300 to receive the customized recommendation service. The request for the autonomous vehicle for exercise may be transmitted through a method of selecting (touching or pressing a button) a display for requesting for the autonomous vehicle displayed on a display window (a screen) of the user terminal 300 by executing the application for the customized recommendation service.

The user information may be information on physical strength including age, health state, body information, disease or not, a current state, and the like. At this time, information on the physiology signal measured by a blood pressure device, a pulse measuring device through the user terminal 300, information input to the user terminal 300 in real time, previously stored information in which the information is stored through an existing membership may be used as the information on the physical strength. Further, the information on the desired exercise may be environmental information including the types of exercise apparatus, exercise intensity, an exercise time, and the like. At this time, information on driving of the exercise apparatus 220 which is currently used according to the exercise schedule, information input to the user terminal 300 in real time, or previously stored information in which information input to the existing membership is stored may be used as the environmental information. Further, the information on the current position may include information on the current position provided by the GPS satellites via the GPS module attached to the autonomous vehicle 200 and the user terminal 300 and geographical information to be displayed on the map. Further, the dynamic situation may be information on the autonomous situation including the dynamic information including road situation, traffic situation, possible arrival time, vehicle speed, the dangerous situation, and the like, which are detected during travelling of the autonomous vehicle from the position of the user to the arrival place.

The server 100 selects the vehicle matching through the vehicle allocation management 130 based on the collected user information, information on the desired exercise, current positions and dynamic situations of the autonomous vehicle 200 and the user terminal 300, and provide the user terminal 300 with a vehicle list indicating a recommended vehicle and a possible arrival time of each vehicle.

At this time, with respect to the selection of the matching vehicle, the vehicle is detected based on the information on the position of the vehicle and the stabilizer for each vehicle through a location tracking service such as geofencing. That is, a possible vehicle is detected by adjusting a level of stability of the stabilizer, and the like, of the vehicle for exercise searched in the predetermined area to be suitable for the type of exercise desired by the user. To this end, a first storage 140a stores information on the position of the vehicle and the stabilizer for each vehicle in advance. Meanwhile, the level of the stabilizer may be determined in advance by dividing the level of the stabilizer into a range of acceleration in which the vehicle may be balanced, a slope of the vehicle, and a reaction speed with respect to a specific event when the exercise is performed during autonomous control. The level of the stabilizer is determined based on the type of the desired exercise. For example, the level of the stabilizer is low in the case of yoga and the level of the stabilizer is normal in the cyber soccer, and the level of the stabilizer is high in the bodybuilding. As described above, the vehicle allocation management 130 may set the level of the stabilizer in advance for each exercise.

In the server 100, the vehicle allocation management 130 allocates allocates the selected vehicle, in the vehicle list, provided to the user terminal 300. The vehicle allocation management 130 transmits the information on the position of the user to the allocated autonomous vehicle 200 and enables the autonomous vehicle to the position of the user through autonomous control (S40). At this time, the travelling of the autonomous vehicle 200 is one embodiment, but is not limited thereto. For example, the information on the position in which the autonomous vehicle 200 is parked is transmitted to the user terminal 300, the user may directly move to the position at which the autonomous vehicle 200 is parked.

Meanwhile, in the server 100, the exercise schedule management 150 generates the exercise schedule by selecting the desired exercise in consideration of the travel route and the traffic situation detected based on the collected information on the position of the user and the arrival place (S50).

At this time, the type of exercise of the exercise apparatus 220 placed in the allocated autonomous vehicle 200 based on the desired exercise to generate at least one candidate exercise schedule based on the information on the user and the environmental information. The exercise set in combination with the type of exercise that may be performed for each section is determined by analyzing road complexity, speed for each section, travel time for each section, and the like based on the travel route and the traffic situation detected by the travel route detector 151 and the traffic situation detector 152. Further, the customized exercise schedule is generated by matching the type of generated exercise set and a method of exercise, among the generated candidate exercise schedule, over time.

Then, the server 100 transmits information on a degree of safe driving including the travel route to the arrival place, the speed for each section, and the customized driving schedule to the autonomous vehicle 200 (S60). That is, the server 100 transmits timing information to adjust the term of exercise according to the route of the autonomous vehicle through exercise scheduling. For example, when safety is maintained, exercise is recommended, and when there is the dangerous element, it is recommended to relax.

As described above, in the server 100, the autonomous control management 190 manages the autonomous control of the autonomous vehicle, and the autonomous vehicle 200 displays the exercise scheduling on the HMI 210 installed in the vehicle during autonomous control (S70).

Then, in the server 100, when the autonomous control proceeds and the dynamic situation occurs according to the situation of the user and the situation of the autonomous control, the dynamic situation processor 171 determines the dangerous situation with reference to the previously stored situation learning model. Further, the exercise set having the exercise effect similar to that of the exercise set checked by the exercise set generator 172 is detected. The detected exercise set is replaced with the corresponding exercise set among the exercise sets included in the customized exercise schedule generated by the exercise schedule corrector 180 to correct the customized exercise schedule (S80).

That is, in the server 100, the situation management 170 receives the identified information on the dynamic situation (a period of time for which the dynamic situation occurs and the exercise set performed while the dynamic situation occurs), and determines the dangerous situation with reference to the previously stored situation learning model. Then, the exercise set corresponding to the dangerous situation determined by the exercise set generator 172 is checked. The exercise set having the exercise effect similar to that of the checked exercise set is detected based on the previously stored information on the exercise knowledge. Then, in the server 100, the exercise schedule corrector 180 replaces the detected exercise set with the corresponding exercise set among the exercise sets included in the customized exercise schedule generated by the exercise schedule management 150, to correct the customized exercise schedule.

The corrected customized exercise schedule may be continually corrected until the autonomous vehicle 200 arrives at the arrival position and may be transmitted to the autonomous vehicle 200. That is, the autonomous vehicle 200 changes the current customized exercise schedule to finally corrected customized exercise schedule always to provide the finally corrected customized exercise schedule.

As described above, according to the present disclosure, it is possible to service the customized exercise schedule through the autonomous vehicle 200 and to suitably cope with the situation of the user and the situation of the autonomous control, thereby improving reliability with respect to the exercise recommendation service during autonomous control.

As various substitutions, changes, and modifications can be made within the scope that does not deviate from the technical idea of the present disclosure for the skilled person in the art to which the present disclosure pertains, the above-described present disclosure is not limited to the above-mentioned embodiment and the accompanying drawings.

The invention claimed is:

1. A system configured to provide a customized recommendation service, comprising:
   autonomous vehicles;
   an exercise apparatus and a human machine interface (HMI) that are installed inside of each of the autonomous vehicles; and
   a server including a transceiver and a processor, the server being configured to:
      receive, by the transceiver from a user terminal of a user, a current position of the user, a destination of the user, physical strength information of the user, and desired exercise information of the user,
      receive, by the transceiver, a current position of each of the autonomous vehicles from each of the autonomous vehicles,
      receive, by the transceiver, traffic information of a travel route between the current position of the user and the destination of the user from a traffic information server,
      select, by the processor, a first autonomous vehicle from among the autonomous vehicles based on the physical strength information, the desired exercise information, the current position of the user, the current position of each of the autonomous vehicles, and the traffic information of the travel route,
      transmit, by the transceiver to the first autonomous vehicle, a control signal for driving the first autonomous vehicle to the current position of the user,
      generate, by the processor, an exercise schedule including exercise sets for sections of the travel route based on the physical strength information, the desired exercise information, a type of the exercise apparatus installed in the first autonomous vehicle, and the traffic information of the travel route, and
      transmit, by the transceiver, the exercise schedule to the first autonomous vehicle,
   wherein the HMI installed in the first autonomous vehicle is configured to output the exercise schedule determined by the server to the user riding in the first autonomous vehicle.

2. The system of claim 1, wherein the traffic information includes a road situation of the travel route, a traffic situation of the travel route, and an estimated arrival time to the destination.

3. The system of claim 1, wherein the physical strength information includes an age of the user, a health state of the user, body information of the user, and information on whether the user has a disease.

4. The system of claim 1, wherein the desired exercise information includes a type of exercise apparatus available to the user, and an exercise intensity and duration desired by the user.

5. The system of claim 1, wherein the server is configured to generate the exercise schedule by matching the exercise sets for each section of the travel route for a driving time of the first autonomous vehicle.

6. The system of claim 1, wherein the exercise apparatus includes at least one of a running machine, a bicycle, a squad equipment, a balance power equipment, a chinning dipping bar, or a weight apparatus.

7. The system of claim 1, wherein the HMI includes a display.

8. A method for providing a customized recommendation service performed by a system including autonomous vehicles, an exercise apparatus and a human machine interface (HMI) that are installed inside of each of the autonomous vehicles, and a server including a transceiver and a processor, the method comprising:
   receiving, by the transceiver from a user terminal of a user, a current position of the user, a destination of the user, physical strength information of the user, and desired exercise information of the user;
   receiving, by the transceiver, a current position of each of the autonomous vehicles from each of the autonomous vehicles;

receiving, by the transceiver, traffic information of a travel route between the current position of the user and the destination of the user from a traffic information server, selecting, by the processor, a first autonomous vehicle from among the autonomous vehicles based on the physical strength information, the desired exercise information, the current position of the user, the current position of each of the autonomous vehicles, and the traffic information of the travel route, transmitting, by the transceiver to the first autonomous vehicle, a control signal for driving the first autonomous vehicle to the current position of the user, generating, by the processor, an exercise schedule including exercise sets for sections of the travel route based on the physical strength information, the desired exercise information, a type of the exercise apparatus installed in the first autonomous vehicle, and the traffic information of the travel route, and transmitting, by the transceiver, the exercise schedule to the first autonomous vehicle, wherein the HMI installed in the first autonomous vehicle is configured to output the exercise schedule to the user riding in the first autonomous vehicle.

9. The method of claim 8, wherein the traffic information includes a road situation of the travel route, a traffic situation of the travel route, and an estimated possible arrival time to the user's destination.

10. The method of claim 8, wherein the physical strength information includes an age of the user, a health state of the user, body information of the user, and information on whether the user has a disease.

11. The method of claim 8, wherein the desired exercise information includes a type of exercise apparatus available to the user, and an exercise intensity and time duration desired by the user.

12. The method of claim 8, wherein the exercise schedule is generated by matching the exercise sets for each section of the travel route for a driving time of the first autonomous vehicle.

13. The method of claim 8, wherein the exercise apparatus includes at least one of a running machine, a bicycle, a squad equipment, a balance power equipment, a chinning dipping bar, or a weight apparatus.

14. The method of claim 8, wherein the HMI includes a display.

* * * * *